(12) United States Patent  (10) Patent No.: US 7,419,974 B2
Bovy et al.  (45) Date of Patent: *Sep. 2, 2008

(54) CYCLOHEXYL(ALKYL)PROPANOLAMINES, PREPARATION METHOD AND PHARMACEUTICAL COMPOSITIONS CONTAINING SAME

(75) Inventors: Philippe R. Bovy, Mareil Marly (FR);
Roberto Cecchi, Lodi (IT); Gilles Courtemanche, Le Plessis Robinson (FR); Tiziano Croci, Milan (IT);
Ambrogio Oliva, Sarrono (IT); Nunzia Viviani, Cantu (IT)

(73) Assignee: Sanofi-Aventis, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 11/464,537

(22) Filed: Aug. 15, 2006

(65) Prior Publication Data

US 2007/0015745 A1  Jan. 18, 2007

Related U.S. Application Data

(63) Continuation of application No. 10/432,493, filed as application No. PCT/FR01/03784 on Nov. 30, 2001.

(30) Foreign Application Priority Data

Nov. 30, 2000  (FR) .................. 00 15477

(51) Int. Cl.
*A61K 31/216* (2006.01)
*A61K 31/423* (2006.01)
*A61K 31/553* (2006.01)
*A61K 31/401* (2006.01)

(52) U.S. Cl. .................. 514/211.09; 514/375; 514/534; 514/423

(58) Field of Classification Search ................ 514/569, 514/605, 211.09
See application file for complete search history.

(56) References Cited

U.S. PATENT DOCUMENTS 4,004,028 A  1/1977  Kaiser
5,096,908 A  3/1992  Gidda et al.

(Continued)

FOREIGN PATENT DOCUMENTS

EP  0345056  12/1989

(Continued)

OTHER PUBLICATIONS

Abitayeh, et al. "New tocolytic agents", Eur. Clinics Obstet. Gynaecol. (2005) 1: 29-35.*

(Continued)

*Primary Examiner*—Rebecca L Anderson
*Assistant Examiner*—Michael P Barker
(74) *Attorney, Agent, or Firm*—Jiang Lin

(57) ABSTRACT

The present invention relates to the compounds of formula (I):

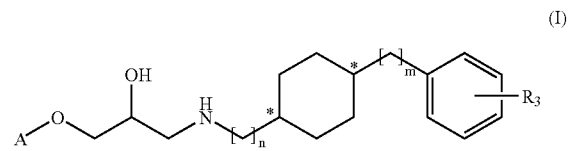

in which A is a group of formula (a) or (b)

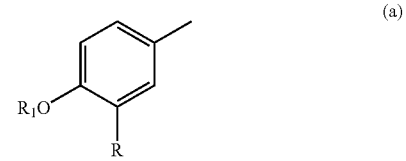

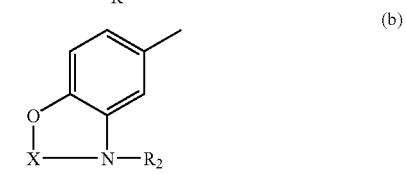

in which R represents a hydrogen or halogen atom, an $—S(O)_z(C_1-C_4)$alkyl group, an $—NHSO_2(C_1-C_4)$alkyl group, an $—SO_2NH(C_1-C_4)$alkyl group, an $—NHSO_2$phenyl-$(C_1-C_4)$alkyl group or an $—NHSO_2$phenyl group, said phenyl possibly being substituted with a halogen atom, with a $(C_1-C_4)$alkyl group or with a $(C_1-C_4)$alkoxy group; $R_1$ represents a hydrogen atom or a $(C_1-C_4)$alkyl group, a $—CO(C_1-C_4)$alkyl group, a phenyl-$(C_1-C_4)$alkyl group or a $—CO$phenyl group, said phenyl also possibly being substituted with a halogen atom or with a $(C_1-C_4)$ alkoxy group; $R_2$ is a hydrogen atom or an $—SO_2(C_1-C_4)$ alkyl group, an $—SO_2$phenyl-$(C_1-C_4)$alkyl group or an $—SO_2$phenyl group; X completes a ring of 5 to 8 atoms, said ring being saturated or unsaturated, possibly being substituted with one or two $(C_1-C_4)$alkyl groups and bearing one or two carbonyl groups; n, m and z are, independently, 0, 1 or 2; $R_3$ represents a hydrogen or halogen atom, a $(C_1-C_6)$alkyl group, a $(C_1-C_4)$alkoxy group, a $—COO(C_1-C_4)$alkyl group, a $—CO(C_1-C_4)$alkyl group, an $—NHSO_2(C_1-C_4)$alkyl group, an $—NHSO_2$phenyl-$(C_1-C_4)$alkyl groups, $—NO_2$, $—CN$, $—CONR_4R_5$, $—COOH$, or a 4,5-dihydro-1,3-oxazol-2-yl or 4,4-dimethyl-4,5-dihydro-1,3-oxazol-2-yl group; $R_4$ and $R_5$ represent, independently, a hydrogen atom, a phenyl, a $(C_1-C_4)$alkyl group or a phenyl-$(C_1-C_4)$alkyl group or $R_4$ and $R_5$ with the nitrogen atom to which they are attached, may form a ring of 5 to 7 atoms in total; and to the salts or solvates thereof, to the pharmaceutical compositions containing them, to a process for the preparation thereof and to intermediates in this process.

12 Claims, No Drawings

U.S. PATENT DOCUMENTS

| | | | |
|---|---|---|---|
| 5,158,956 | A | 10/1992 | Gidda et al. |
| 5,258,379 | A | 11/1993 | Gidda et al. |
| 5,340,838 | A | 8/1994 | Gidda et al. |
| 5,457,120 | A | 10/1995 | Gidda et al. |
| 5,532,244 | A | 7/1996 | Wong et al. |
| 5,532,250 | A | 7/1996 | Wong et al. |
| 5,532,264 | A | 7/1996 | Wong et al. |
| 5,532,268 | A | 7/1996 | Wong et al. |
| 5,538,992 | A | 7/1996 | Wong et al. |
| 5,552,429 | A | 9/1996 | Wong et al. |
| 5,576,352 | A | 11/1996 | Gidda et al. |
| 5,594,025 | A | 1/1997 | Gidda et al. |
| 5,594,034 | A | 1/1997 | Gidda et al. |
| 5,776,969 | A | 7/1998 | James |
| 5,958,429 | A | 9/1999 | Wong |
| 6,169,105 | B1 | 1/2001 | Wong et al. |
| 6,730,792 | B2 | 5/2004 | Evers et al. |
| 6,890,955 | B2 | 5/2005 | Hadri et al. |
| 2002/0019440 | A1 | 2/2002 | Philippe et al. |
| 2003/0191156 | A1 | 10/2003 | Evers et al. |
| 2004/0053916 | A1 | 3/2004 | Bovy et al. |
| 2004/0242633 | A1 | 12/2004 | Evers et al. |
| 2005/0176731 | A1 | 8/2005 | Bovy et al. |
| 2005/0239836 | A1 | 10/2005 | John et al. |
| 2006/0100283 | A1 | 5/2006 | Bovy et al. |

FOREIGN PATENT DOCUMENTS

| | | |
|---|---|---|
| EP | 642787 | 3/1995 |
| JP | 2000086603 | 3/2000 |
| JP | WO 02/00622 A2 * | 1/2002 |
| WO | WO 94/11386 | 5/1994 |
| WO | WO 97/31629 | 9/1997 |
| WO | WO 9831357 | 7/1998 |
| WO | WO 99/65895 | 12/1999 |
| WO | WO 00/38685 | 7/2000 |
| WO | WO 00/40561 | 7/2000 |
| WO | WO 02/058697 | 8/2002 |
| WO | WO 03/099772 | 12/2003 |
| WO | WO 2004/006849 | 1/2004 |
| WO | WO 2004/019932 | 3/2004 |
| WO | WO 2004/076413 | 9/2004 |

OTHER PUBLICATIONS

Bardou, et al. "Functional, biochemical and molecular biological evidence for a possible B3-adrenoceptor in human near-term myometrium", British Journal of Pharmacology (2000) 130: 1960-1966.*

Hoffstedt, et al. "Determination of beta 3-adrenoceptor mediated lipolysis in human fat cells", Obesity Research (1995) 3: 447-457. Abstract only.*

Weyer, et al. "Development of beta3-adrenoceptor agonists for the treatment of obesity and diabetes—an update", Diabetes & Metabolism (Paris) (1999) 25: 11-21.*

Collins, et al. "Strain-Specific Response to β3-Adrenergic Receptor Agonist Treatment of Diet-Induced Obesity in Mice", Endocrinology, vol. 138(1), pp. 405-413 (1997).*

Sum, et al. "Prodrugs of CL316243: A Selective β3-Adrenergic Receptor Agonist for Treating Obesity and Diabetes", Bioorganic & Medicinal Chemistry Letters, vol. 9, pp. 1921-1926 (1999).*

Sasaki, et al. "Anti-Obesity Effects of Selective Agonists to the β3-Adrenergic Receptor in Dogs. II. Recruitment of Thermogenic Brown Adipocytes and Reduction of Adiposity after Chronic Treatment with a β3-Adrenergic Agonist", Japanese Society of Veterinary Science, vol. 60(4), pp. 465-469 (1998).*

Rathi, et al. "Functional and Molecular Characterization of Beta Andreoceptors in the Internal Anal Sphincter", Journal of Pharmacology and Experimental Therapeutics, vol. 305(2), pp. 615-624 (2003).*

ClinicalTrials.gov, "A Study to Investigate GW427353 In Subjects with Irritable Bowel Syndrome (IBS)", NCT00394186 (2008).*

Dennedy, et al. "β2 and β3-Adrenoceptor agonists: Human myometrial selectivity and effects on umbilical artery tone", Am. J. Obstet. Gynecol., vol. 187(33), pp. 641-647 (2002).*

Croci, et al. "In Vitro and in Vivo Pharmacological Characterization of Ethyl-4-{trans-4-[((2S)-2-hydroxy-3-{4-hydroxy-3[(methylsulfonyl)amino]-phenoxy}propyl) Amino]cyclohexyl}benzoate Hydrochloride (SAR150640), a New Potent and Selective Human β3-Adrenoceptor Agonist for the Treatment of Preterm Labor", J. Pharm. Exp. Ther., vol. 321, 2007.*

Fletcher, et al., "Beta-3 Adrenergic Receptor Agonists Cause an Increase in Gastrointestinal Transit Time in Wild-type Mice, But Not in Mice Lacking the Beta-3 Adrenergic Receptor", Journal of Pharmacology and Experimental Therapeutics, vol. 287, pp. 720-724 (1998).*

Martin, C., et al., Beta3-adrenoceptor agonists, BRL 37344 and SR 58611A, do not induce relaxation of human, sheep and guinea-pig airway smooth muscle in vitro, Eur Respir J., 1994, 7, 1610-1615.

* cited by examiner

CYCLOHEXYL(ALKYL)PROPANOLAMINES, PREPARATION METHOD AND PHARMACEUTICAL COMPOSITIONS CONTAINING SAME

This application is a Continuation of U.S. application Ser. No. 10/432,493, filed May 21, 2003, which is a National Stage Application of International Application No. PCT/FR01/03784, filed Nov. 30, 2001.

The present invention relates to novel cyclohexyl(alkyl)propanolamines, to the pharmaceutical compositions containing them, to a process for the preparation thereof and to synthesis intermediates in this process.

WO 99/65895 describes phenoxypropanolamines in which the amine bears a substituted piperidine, these compounds showing agonist activity with respect to the beta-3 adrenergic receptor.

The beta-3 adrenergic receptor has been the subject of many studies aimed at synthesizing compounds which are agonists with respect to this receptor, these compounds exerting a considerable anti-obesity and anti-diabetic effect in humans, as described, for example, by Weyer, C et al., Diabetes Metab., 1999, 25(1):11-21.

It has now been found that certain propanolamines bearing a cyclohexyl(alkyl) group on the amine possess a powerful agonist activity with respect to beta-3 adrenergic receptors.

Thus, the present invention relates, according to one of its aspects, to cyclohexyl(alkyl)propanolamines of formula (I):

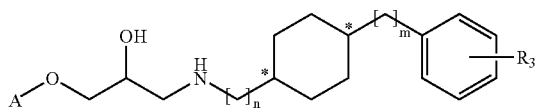
(I)

in which

A is a group of formula (a) or (b)

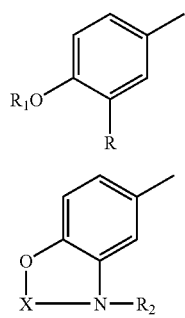

where

R represents a hydrogen or halogen atom, an $-S(O)_z(C_1-C_4)$alkyl group, an $-NHSO_2(C_1-C_4)$alkyl group, an $-SO_2NH(C_1-C_4)$alkyl group, an $-NHSO_2$phenyl-$(C_1-C_4)$alkyl group or an $-NHSO_2$phenyl group, said phenyl possibly being substituted with a halogen atom, with a $(C_1-C_4)$alkyl group or with a $(C_1-C_4)$alkoxy group;

$R_1$ represents a hydrogen atom or a $(C_1-C_4)$alkyl group, a $-CO(C_1-C_4)$alkyl group, a phenyl-$(C_1-C_4)$alkyl group or a $-CO$-phenyl group, said phenyl possibly being substituted with a halogen atom or with a $(C_1-C_4)$alkoxy group;

$R_2$ is a hydrogen atom, an $-SO_2(C_1-C_4)$alkyl group, an $-SO_2$phenyl-$(C_1-C_4)$alkyl group or an $-SO_2$phenyl group;

X completes a ring of 5 to 8 atoms, said ring being saturated or unsaturated, possibly being substituted with one or two $(C_1-C_4)$alkyl groups and bearing one or two carbonyl groups;

n, m and z are, independently, 0, 1 or 2;

$R_3$ represents a hydrogen or halogen atom, a $(C_1-C_6)$alkyl group, a $(C_1-C_4)$alkoxy group, a $-COO(C_1-C_4)$alkyl group, a $-CO-(C_1-C_4)$alkyl group, an $-NHSO_2(C_1-C_4)$alkyl group, an $-NHSO_2$phenyl-$(C_1-C_4)$alkyl group, $-NO_2$, $-CN$, $-CONR_4R_5$, $-COOH$, or a 4,5-dihydro-1,3-oxazol-2-yl or 4,4-dimethyl-4,5-dihydro-1,3-oxazol-2-yl group;

$R_4$ and $R_5$ represent, independently, a hydrogen atom, a phenyl, a $(C_1-C_4)$alkyl group or a phenyl-$(C_1-C_4)$alkyl group; or $R_4$ and $R_5$ with the nitrogen atom to which they are attached, may form a ring of 5 to 7 atoms in total;

and the salts or solvates thereof.

In the present description, the terms "$(C_1-C_4)$alkyl" and "$(C_1-C_6)$alkyl" denote monovalent radicals formed from a respectively $C_1-C_4$ and $C_1-C_6$ hydrocarbon containing a straight or branched saturated chain.

In the present description, the term "halogen" denotes an atom chosen from chlorine, bromine, iodine and fluorine.

Preferred compounds are those in which n and m are each zero.

Other preferred compounds are those in which $R_1$ is a hydrogen atom.

Other preferred compounds are those in which R is chosen from an $-NHSO_2(C_1-C_4)$alkyl group, an $-NHSO_2$phenyl-$(C_1-C_4)$alkyl group or an $-NHSO_2$phenyl group.

Other preferred compounds are those in which $R_3$ is $-COO(C_1-C_4)$alkyl or $-CO(C_1-C_4)$alkyl or $CONR_4R_5$.

Other preferred compounds are those in which $R_3$ is in position 4 of the benzene.

Other preferred compounds are those in which z is 2.

Other preferred compounds are those in which X is a methylene, an ethylene or a propylene.

Other preferred compounds are those in which X is a carbonyl, a $-CO-CO-$ group, a $-CO-C((C_1-C_4)$alkyl$)_2-CO-$ group, a methylene monosubstituted or disubstituted with $(C_1-C_4)$alkyl or a $-COCH_2-$ group.

Preferred $-NHSO_2$phenyl-$(C_1-C_4)$alkyl and $-SO_2$phenyl-$(C_1-C_4)$alkyl groups are, respectively, benzylsulphonylamino and benzylsulphonyl.

When $R_4$ and $R_5$ form, with the nitrogen atom to which they are attached, a ring of 5 to 7 atoms, preferred rings are piperidine and pyrrolidine.

The salts of the compounds of formula (I) according to the present invention comprise both the addition salts with pharmaceutically acceptable inorganic or organic acids, such as hydrochlorate, hydrobromate, sulphate, hydrogen sulphate, dihydrogen phosphate, citrate, maleate, tartrate, fumarate, gluconate, methanesulphonate, 2-naphtalenesulphonate, etc., and the addition salts which allow suitable separation or crystallization of the compounds of formula (I), such as picrate or oxalate, or the addition salts with optically active acids, for example, camphosulphonic acids and mandelic or substituted mandelic acids.

When the compounds of formula (I) have a free carboxyl group, the salts also comprise the salts with inorganic bases, preferably those with alkaline metals such as sodium or potassium, or with organic bases.

The optically pure stereoisomers, and also the mixtures of isomers of the compounds of formula (I), due to the asymmetric carbon, in any proportion, are also part of the present invention.

Preferred compounds of formula (I) are the compounds in which the configuration of the carbon of the propanolamine bearing the OH group is (S).

The compounds of formula (I) may be in the form of "cis" or "trans" geometrical isomers, depending on the relative position of the substituents in positions 1 and 4 of the cyclohexyl ring (marked with a star). These pure isomers and their mixtures, in any proportion, are part of the present invention.

The mixtures of optical and geometrical stereoisomers above, in any proportion, are also part of the present invention.

The compounds of formula (I) may be prepared by treating a compound of formula (II):

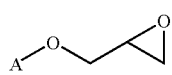

(II)

in which A is as indicated above, with an amine of formula (III)

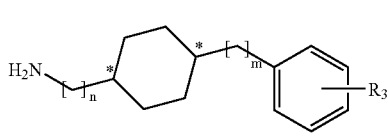

(III)

in which n, m and $R_3$ are as defined above and, optionally, transforming the compound of formula (I) thus obtained into a salt or solvate thereof.

More particularly, the reaction between the compounds of formulae (II) and (III) is carried out in an organic solvent, such as a lower alcohol, for instance methanol, ethanol, isopropanol and tert-butanol; dimethyl sulphoxide; a linear or cyclic ether; an amide such as dimethylformamide or dimethylacetamide or mixtures of these solvents; preferably using at least equimolecular amounts of the reagents.

The temperature of the reaction is between room temperature and the reflux temperature of the solvent chosen.

When $R_1$ represents hydrogen, it is preferable to protect the functional group with a protective group in order to increase the yield of the reaction. As protective groups, use may be made of the protective groups which are conventional for phenol groups, such as for example methoxyethoxymethyl (MEM), trimethylsilylethoxymethyl (SEM), benzyl, optionally substituted, or benzoyl, according to well-known techniques.

Other functional groups optionally present (amino groups for example) may, themselves, also be protected by suitable protective groups according to well-known conventional techniques.

The compounds of formula (II) are compounds which are known in the literature or they may be prepared using processes similar to described processes.

The compounds of formula (III) may be prepared using an intermediate of formula (IX) obtained according to the following Scheme 1.

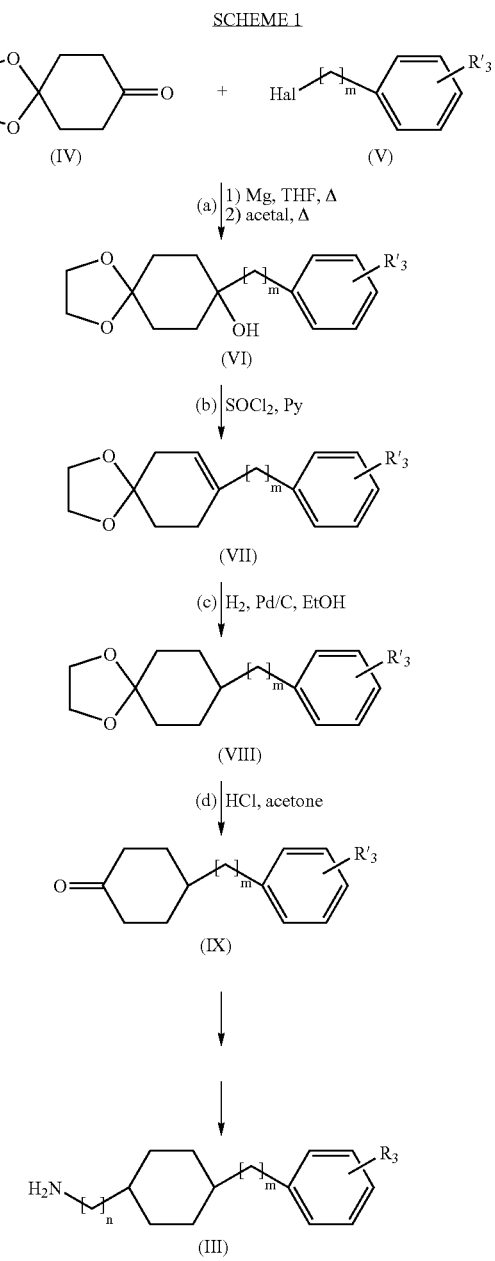

In the formulae of Scheme 1, m is as defined above and Hal represents a halogen, preferably bromine, while $R'_3$ is a 4,5-dihydro-1,3-oxazol-2-yl, 4,4-dimethyl-4,5-dihydro-1,3-oxazol-2-yl, $(C_1-C_4)$alkyl or $(C_1-C_4)$alkoxy group.

These are reactions which are well-known to those skilled in the art; the condensation step may, for example, be carried out in a way similar to that described by Meyers et al., J. Org. Chem., 1974, 39: 2787. The intermediate alcohol (VI) is transformed into the derivative (VII), for example according to the method described in A. M. Gonzales-Cameno et al., Tetrahedron, 1994, 50: 10971 or with $POCl_3$ as described in Org. Prep. Proced. Int., 1995, 27: 122, and then into the saturated derivative (VIII) via a conventional reduction reaction. The hydrolysis of the actual group may be carried out in a way similar to the reaction described by C. Szantay et al., Tetrahedron, 1996, 52(33): 11053.

The intermediate of formula (IX) may be used to prepare the compounds of formula (III) by transforming, for example, the carbonyl group of the cyclohexane into an amino group by reduction of the corresponding oxime or, when n is 1 or 2, into an aminoalkyl group by reaction with a cyanide or nitromethane, or by the Wittig reaction with the desired phosphonate, according to well-known reactions.

When $R'_3$ is a 4,5-dihydro-1,3-oxazol-2-yl or 4,4-dimethyl-4,5-dihydro-1,3-oxazol-2-yl group, the compound of formula (III) in which $R_3$ is —COOH is easily obtained by hydrolysis.

Most of the compounds of formula (III), such as for example those in which $R_3$ is —CN, —CO($C_1$-$C_4$)alkyl, —COO($C_1$-$C_4$)alkyl, a sulphonamido group, a halogen atom or —$NO_2$, may then be obtained by transformation of the compound of formula (III) in which $R_3$ is —COOH, according to reactions well-known to those skilled in the art, after protection of the $NH_2$ group with a protective group such as, for example, the BOC group and/or benzyl.

Alternatively, use may be made, as a starting product, of the compound of formula (V) in which $R'_3$ is —CN, and m=0,1; in this case, the condensation of step (a) is carried out as described, for example, in J. Med. Chem., 1992, 35: 320 and the product (III) obtained at the end of the process above is easily transformed into the derivatives in which $R_3$ is —COOH, —CO($C_1$-$C_4$)alkyl or —$CONR_4R_5$, after protection of the $NH_2$ group with a protective group such as, for example, the BOC (tert-butoxycarbonyl) group and/or benzyl.

The "cis" and "trans" isomers may be obtained by separation of the mixture, for example by chromatography or by selective crystallization, according to conventional processes.

The activity of the compounds of the present invention with respect to beta-3 activity was demonstrated using in vitro tests on human colon according to the method described by T. Croci et al., Br. J. Pharmacol., 1997, 122: 139P, by L. Manara et al., Gut, 2000, 47: 337-342 and in EP-B-436435.

More particularly, it was noted that the compounds of formula (I) are much more active on the isolated colon than on the atrium and on the trachea.

These surprising properties of the compounds of formula (I) make it possible to envisage their use as medicinal products with beta-3 agonist action.

In addition, the compounds of formula (I) are relatively nontoxic; in particular, their acute toxicity is compatible with their use as medicinal products for treating diseases in which compounds having an affinity for the beta-3 receptor, in particular beta-3 agonists, are of use. Such diseases are described in the literature. The compounds of formula (I), and also the pharmaceutically acceptable salts thereof, may therefore, for example, be indicated in the treatment of gastrointestinal diseases such as inflammatory diseases of the intestine, for instance irritable bowel disease (IBD), as modulators of intestinal motivity, as lipolytic agents, anti-obesity agents, antidiabetic agents, psychotropic agents, anti-glaucoma agents, cicatrizing agents and anti-depressants, as inhibitors of uterine contractions, as tocolytics for preventing or delaying preterm births, and for the treatment and/or prophylaxis of dysmenorrhoea. In addition, the compounds of formula (I) may be used in the treatment of certain diseases of the central nervous system, such as for example depression, and also of certain disorders of the urinary system, such as urinary incontinence.

The use of compounds of formula (I) above, and also that of the pharmaceutically acceptable salts and solvates thereof, for preparing the medicinal products above, constitutes a subsequent aspect of the present invention.

For such a use, an effective amount of a compound of formula (I), or of a pharmaceutically acceptable salt or solvate thereof, is administered to the mammals which require such a treatment.

The compounds of formula (I) above, and the pharmaceutically acceptable salts and solvates thereof, may be used at daily doses of 0.01 to 20 mg per kilo of body weight of the mammal to be treated, preferably at daily doses of from 0.1 to 10 mg/kg. In humans, the dose may vary preferably from 0.5 mg to 1500 mg per day, in particular from 2.5 to 500 mg, depending on the age of the individual to be treated, the type of treatment, prophylactic or curative, and the seriousness of the disorder. The compounds of formula (I) are generally administered as a dosage unit of 0.1 to 500 mg, preferably of 0.5 to 100 mg, of active principle, one to five times a day.

Said dosage units are preferably formulated in pharmaceutical compositions in which the active principle is mixed with a pharmaceutical excipient.

Thus, according to another of its aspects, the present invention relates to pharmaceutical compositions containing, as an active principle, a compound of formula (I) above or a pharmaceutically acceptable salt or solvate thereof.

In the pharmaceutical compositions of the present invention for oral, sublingual, subcutaneous, intramuscular, intravenous, topical, transdermal or rectal administration, the active ingredients of formula (I) above, and the pharmaceutically acceptable salts and solvates thereof, may be administered in unit administration forms, mixed with conventional pharmaceutical supports, to animals and humans for treating the abovementioned disorders. The unit administration forms which are suitable comprise oral forms such as tablets, gel capsules, powders, granules and oral solutions or suspensions, sublingual and buccal administration forms, subcutaneous, intramuscular or intravenous administration forms, local administration forms and rectal administration forms.

When a solid composition in the form of tablets is prepared, the main active ingredient is mixed with a pharmaceutical vehicle such as gelatin, starch, lactose, magnesium stearate, talc, gum arabic or the like. The tablets may be coated with sucrose or other suitable materials, or they may be treated such that they have sustained or delayed activity and that they release, in a continuous manner, a predetermined amount of active principle.

A preparation of gel capsules is obtained by mixing the active ingredient with a diluent and pouring the mixture obtained into soft or hard gel capsules.

A preparation in the form of a syrup or elixir may contain the active ingredient together with a sweetener, preferably a calorie-free sweetener. methylparaben and propylparaben as antiseptics, and also a flavour enhancer and a suitable colorant.

The water-dispersible powders or granules may contain the active ingredient mixed with dispersing agents or wetting agents, or suspending agents, such as polyvinylpyrrolidone, and also with sweeteners or flavour correctors.

For local administration, the active principle is mixed into an excipient for preparing creams or ointments, or it is dissolved in a vehicle for intraocular administration, for example, in the form of an eyewash.

For rectal administration, use is made of suppositories prepared with binders which melt at rectal temperature, for example cocoa butter or polyethylene glycols.

For parenteral administration, aqueous suspensions, saline solutions or injectable sterile solutions which contain pharmacologically compatible dispersion agents and/or wetting agents, for example propylene glycol or butylene glycol, are used.

The active principle may also be formulated in the form of microcapsules, optionally with one or more supports or additives.

According to another of its aspects, the present invention relates to a method for treating pathological conditions which are improved by a beta-3 agonist action, which comprises administering a compound of formula (I) or a pharmaceutically acceptable salt or solvate thereof.

The compounds of formula (I), in particular the compounds (I) labelled with an isotope, may also be used as laboratory tools in biochemical assays.

The compounds of formula (I) bind to the beta-3 adrenergic receptor. These compounds may therefore be used in a conventional binding assay, in which an organic tissue in which this receptor is particularly abundant is used, and the amount of compound (I) displaced by a test compound is measured, in order to evaluate the affinity of said compound with respect to the binding sites of this particular receptor.

Another specific subject of the present invention is therefore a reagent which can be used in biochemical assays, which comprises at least one suitably labeled compound of formula (I).

The following examples illustrate the invention more clearly, in these examples, the following abbreviations may be used:

Ph=phenyl; Bn=benzyl; Me=methyl; Et=ethyl; Bu=butyl; Ox=4,4-dimethyl-4,5-dihydro-1,3-oxazol-2-yl.

PREPARATION 1

Ethyl 4-(4-oxocyclohexyl)benzoate (i) 8-[4-(4,4-Dimethyl-4,5-dihydro-1,3-oxazol-2-yl)phenyl]-1,4-dioxaspiro[4,5]decan-8-ol A solution of 8 g of 2-(4-bromophenyl)-4,4-dimethyl-4,5-dihydro-1,3-oxazole (31.5 mmol) in 15 ml of anhydrous THF is poured dropwise onto 956 mg of Mg (39.3 mmol) in such a way as to maintain the mixture at the reflux temperature and the mixture is refluxed for 2.5 hours. The mixture is cooled to room temperature and a solution of 5.41 g of 1,4-cyclohexandione monoethyleneacetal (34.65 mmol) in 20 ml of anhydrous THF is added to it dropwise. The mixture is stirred at room temperature for 1.5 hours and then at reflux temperature for 1 hour. The mixture is poured into 500 ml of a 10% $NH_4Cl$ solution and extracted with ethyl acetate. The organic phase is dried and, after filtration, the solvent is evaporated off under reduced pressure. The residue is crystallized in ethyl acetate. The product of the title is obtained in the form of a white solid.

M.p. 146-148° C.

(ii) 2-[4-(1,4-Dioxaspiro[4,5]dec-7-en-8-yl)phenyl]-4,4-dimethyl-4,5-dihydro-1,3-oxazole 73.5 ml of pyridine are added to a solution of 34 g of the product of the previous step (102.6 mmol) in 250 ml of methylene chloride; the mixture is cooled to 0° C. and 15 ml of thionyl chloride (205 mmol) are added to it dropwise over 15 minutes. After one hour, the cooling bath is removed and, one hour later, the mixture is refluxed for one hour. The solvent is evaporated off and 400 ml of water and 250 ml of ethyl acetate are added. The organic phase is washed with a saturated aqueous NaCl solution. The aqueous phase is extracted with ethyl acetate, the pooled organic phases are dried and, after filtration, the solvent is evaporated off under reduced pressure. The product of the title is obtained in the form of a white solid which is crystallized in an ethyl acetate/hexane mixture.

M.p. 109-111° C.

(iii) 2-[4-(1,4-Dioxaspiro[4,5]dec-8-yl)phenyl]-4,4-dimethyl-4,5-dihydro-1,3-oxazole A solution of 33.1 g of the product of the previous step (105.6 mmol) in 350 ml of absolute ethanol is hydrogenated in the presence of 4.0 g of Pd/C at 10%, at a pressure of 1 atmosphere and at 30° C., for 5 hours. The catalyst is filtered and the solvent is evaporated off. The residue is taken up in hexane and a white solid is filtered off. The compound of the title is thus obtained.

M.p. 128-140° C.

(iv) Ethyl 4-(4-oxocyclohexyl)benzoate 3 g of the product of step (iii) (9.51 mmol) are dissolved in 60 ml of ethanol and 4.0 ml of 96% sulphuric acid are added, and the mixture is refluxed for 22 hours. The solvent is partially evaporated off and the remaining mixture is taken up with a mixture of 300 ml of a saturated sodium bicarbonate solution and 150 ml of ethyl acetate. The organic phase is washed with a saturated aqueous NaCl solution. The organic phase is dried and, after filtration, the solvent is evaporated off under reduced pressure. The crude product is purified by chromatography on a silica gel column, eluting with an 8/2 hexane-ethyl acetate mixture. The compound of the title is obtained in the form of a solid.

M.p. 60-62° C.

PREPARATION 2

4-[4-(4,4-Dimethyl-4,5-dihydro-1,3-oxazol-2-yl)phenyl]cyclohexanone 2 g of the product of step (iii) of Preparation 1 (6.34 mmol) are dissolved in 70 ml of acetone and 4 ml of 6N hydrochloric acid are added to this. The mixture is stirred at room temperature for 20 hours. The solvent is evaporated off and the residue is taken up with a mixture of 250 ml of a 5% sodium bicarbonate solution and 200 ml of ethyl acetate. The organic phase is washed with water and with a saturated aqueous NaCl solution. The organic phase is dried and, after filtration, the solvent is evaporated off under reduced pressure. The crude product is purified by chromatography on a silica gel column, eluting with a 6/4 hexane/ethyl acetate mixture. The compound of the title is obtained in the form of a white solid.

M.p. 118-120° C.

PREPARATION 3

Ethyl 4-(4-aminocyclohexyl)benzoate (cis and trans) and hydrochlorate of the trans isomer (i) Ethyl 4-[4-(methoxyimino)cyclohexyl]benzoate 2.88 g of the product of preparation 1 (11.7 mmol) are dissolved in 25 ml of ethanol and 1.17 g of O-methyl-hydroxylamine (14 mmol) and 5 ml of pyridine are added to this. The mixture is stirred at 50° C. for 4 hours. The solvent is evaporated off and the residue is taken up with a mixture of 50 ml of water and 50 ml of ethyl acetate. The organic phase is washed with water and with a saturated aqueous NaCl solution. The organic phase is dried and, after filtration, the solvent is evaporated off under reduced pressure. The crude product is purified by chromatography on a silica gel column, eluting with a 90/10 hexane/ethyl acetate mixture. The compound of the title is obtained in the form of a white solid.

M.p. 74-76° C.

(ii) Ethyl 4-(4-aminocyclohexyl)benzoate (cis and trans) and hydrochlorate of the trans isomer 1.42 g of the product of the previous step (5.16 mmol) are dissolved in 5 ml of THF, in a nitrogen atmosphere at 0° C., and 11.3 ml of a 1M solution of boron hydride in THF (11.3 mmol) are added over 10 minutes. The mixture is stirred for 5 h at room temperature and then at reflux temperature for 1 hour, 30 ml of ethanol are added to the mixture, which is stirred for 1 hour at reflux temperature, and then 3 ml of ethanol saturated with hydrochloric acid are added to this, followed by stirring at 70° C. for 2 hours. The solvent is evaporated off and the residue is taken up with a mixture of 40 ml of a saturated sodium bicarbonate solution and 40 ml of ethyl acetate. The organic phase is washed with a saturated aqueous NaCl solution. The organic phase is dried and, after filtration, the solvent is evaporated off under reduced pressure. The crude product is purified by chromatography on a silica gel column, eluting with a 94/6/0.6 methyl chloride/methanol/$NH_4OH$ mixture. The "trans" compound of the title is obtained in the form of a white solid.

M.p. 98-103° C.

The hydrochlorate of this compound is obtained by treating it with a solution of hydrochloric acid in ethanol.

M.p. 305-308° C.

The "cis" compound of the title is obtained in the form of a solid.

M.p. 46-48° C.

PREPARATION 4

4-Benzyloxy-1-((2S)2,3-epoxypropoxy)-3-(N-phenylsulphonyl-N-tert-butoxycarbonylamino)benzene (i) 4-Benzyloxy-3-(phenylsulphonylamino)phenyl acetate A mixture of 5.0 g (0.0194 mol) of 4-benzyloxy-3-aminophenyl acetate, 3.3 ml (0.0236 mol) of triethylamine and 3.0 ml (0.0236 mol) of benzenesulphonyl chloride in 150 ml of methylene chloride is stirred at room temperature overnight. The mixture is then washed with water and the organic phase is dried, followed by purification by chromatography on a silica gel column, eluting with a 7/3 cyclohexane/ethyl acetate mixture. The compound of the title is obtained.

M.p. 109-111° C.

(ii) 4-Benzyloxy-3-(N-tert-butoxycarbonyl-N-phenylsulphonylamino)phenyl acetate

A mixture of 5.4 g (0.0136 mol) of the product of the previous step, 3.6 g (0.0163 mol) of di-tert-butyl dicarbonate and 0.33 g (0.00272 mol) of 4-dimethylaminopyridine in 100 ml of methylene chloride is stirred at room temperature overnight. The solvent is then evaporated off and the product of the title thus obtained is recrystallized in ethyl acetate.

M.p. 172-174° C.

(iii) 4-Benzyloxy-3-(N-tert-butoxycarbonyl-N-phenylsulphonylamino)phenol

A mixture of 3.8 g (0.0076 mol) of the product of the previous step in 200 ml of methanol and 9.1 ml of a 1M NaOH solution is stirred at room temperature for 40 minutes. Citric acid is then added until a pH of 6 is obtained and the solvent is evaporated off. The residue is taken up in methylene chloride and washed with water, the organic phase is dried, the solvent is evaporated off and the product is treated in isopropyl ether. The compound of the title is obtained.

M.p. 170-172° C.

(iv) 4-Benzyloxy-1-((2S)2,3-epoxypropoxy)-3-(N-phenylsulphonyl-N-tert-butoxycarbonylamino)benzene A mixture of 2.9 g (0.0063 mol) of the product of the previous step, 2.9 g of crushed potassium carbonate and 2.0 g (0.0078 mol) of (2S)(+)glycidyl nosylate in 150 ml of acetone is stirred at reflux temperature overnight. The mixture is filtered, the solvent is evaporated off and the residue is purified by chromatography on a silica gel column, eluting with an 8/2 cyclohexane/ethyl acetate mixture. The compound of the title is obtained, which is recrystallized in ethyl acetate.

M.p. 152-154° C.

PREPARATION 5

4-Benzyloxy-3-(N-n-butylsulphonyl-N-tert-butoxycarbonylamino)-1-((2S)2,3-epoxypropoxy)benzene The compound of the title is obtained by carrying out the procedure as described in Preparation 4, but using n-butylsulphonyl chloride instead of benzenesulphonyl chloride.

M.p. 88-90° C.

PREPARATION 6

4-Benzyloxy-3-(N-benzylsulphonyl-N-tert-butoxycarbonylamino)-1-((2S)2,3-epoxypropoxy)benzene The compound of the title is obtained by carrying out the procedure as described in Preparation 4, but using benzylsulphonyl chloride instead of benzenesulphonyl chloride.

M.p. 123-125° C.

PREPARATION 7

4-Benzyloxy-1-((2S)2,3-epoxypropoxy)-3-(N-methylsulphonyl-N-benzylamino)benzene (i) 4-Benzyloxy-3-(N-methylsulphonyl-N-benzylamino)phenyl acetate A mixture of 7.7 g (0.023 mol) of 4-benzyloxy-3-(N-methylsulphonylamino)phenyl acetate, 4.75 g (0.035 mol) of crushed potassium carbonate and 3.3 ml (0.0276 mol) of benzyl bromide in 150 ml of anhydrous acetone is stirred at reflux temperature for 4 hours. After filtration and evaporation, the compound of the title is obtained, which is recrystallized in ethyl acetate.

M.p. 143-145° C.

(ii) 4-Benzyloxy-3-(N-benzyl-N-methylsulphonylamino)phenol

The compound of the title is obtained by carrying out the procedure described in Preparation 4 (iii), but using the product of the previous step.

M.p. 156-158° C.

(iii) 4-Benzyloxy-1-((2S)2,3-epoxypropoxy)-3-(N-benzyl-N-methylsulphonylamino)benzene The compound of the title is obtained by carrying out the procedure described in Preparation 4 (iv), but using the product of the previous step.

M.p. 112-113° C.

PREPARATION 8 trans-4-(4-Aminocyclohexyl)-N,N-diethylbenzamide (i) trans-Ethyl 4-(4-(N-benzyloxycarbonylamino)cyclohexyl)benzoate A mixture of 2.0 g (0.0008 mol) of trans-ethyl 4-(4-aminocyclohexyl)benzoate, 1.25 ml of triethylamine and 1.26 ml (0.0084 mol) of benzyl chloroformate at 95% in 40 ml of dimethylformamide is stirred at room temperature for 3 hours. The mixture is poured into water, extracted with ethyl acetate and dried, and the solvent is evaporated off. The residue is purified by chromatography on a silica gel column, eluting with an 8/2 cyclohexane/ethyl acetate mixture. The compound of the title is obtained.

M.p. 158-160° C.

(ii) trans-4-(4-(N-Benzyloxycarbonylamino)cyclohexyl) benzoic acid

The ester of the previous step is hydrolysed with a solution of ethanol/tetrahydrofuran in the presence of NaOH. The compound of the title is obtained.

M.p. 249-251° C.

(iii) trans-4-(4-(N-Benzyloxycarbonylamino)cyclohexyl)-N,N-diethylbenzamide

A mixture of 650 mg (1.84 mmol) of the product of the previous step, 814 g (1.84 mmol) of BOP, 0.190 ml (1.84 mmol) of diethylamine and 0.258 ml (1.84 mmol) of triethylamine in 30 ml of methylene chloride is heated at 40° C. for 5 hours and then at room temperature overnight. The solvent is evaporated off and the residue is taken up in ethyl acetate and washed with a sodium bicarbonate solution and then with an aqueous acetic acid solution; the organic phase is dried and the solvent is evaporated off. The residue is purified by chromatography on a silica gel column, eluting with a 1/1 cyclohexane/ethyl acetate mixture. The compound of the title is obtained.

M.p. 122-125° C.

(iv) trans-4-(4-Aminocyclohexyl)-N,N-diethylbenzamide

A solution of 610 mg of the product of the previous step in 20 ml of ethanol is stirred at a temperature of 40° C. in a hydrogen atmosphere for 7 hours in the presence of 70 mg of Pd/C at 10%. The catalyst is filtered and the solvent is evaporated off under reduced pressure, and the product is treated with ethyl ether. The compound of the title is obtained.

M.p. 180-182° C.

PREPARATION 9 trans-4-(4-Aminocyclohexyl)-N-butylbenzamide

The compound of the title is obtained by carrying out the procedure as described in Preparation 8 (iii) and (iv), but using n-butylamine instead of diethylamine.

M.p. 108-110° C.

PREPARATION 10 trans-(4-N-Benzylaminocyclohexyl)benzene 5.0 g of 4-phenylcyclohexanone (0.028 mol), 3.32 g of benzylamine (0.031 mol), 2.14 g of NaBH$_3$CN (0.034 mol) (added at 0° C.) and 3.75 g of acetic acid in 100 ml of ethanol are mixed and stirred overnight at room temperature. A 1N sodium bicarbonate solution is then added, the mixture is stirred at room temperature for 3 hours, the ethanol is evaporated off, the remainder is extracted with ethyl acetate and the solvent is evaporated off. The product is dissolved in ethanol, a 3N HCl/ethanol solution is added to this and the mixture is stirred for 3 hours. It is brought to basic pH with a 1N sodium bicarbonate solution, the ethanol is evaporated off and, after extraction with ethyl acetate, the organic phase is dried and the solvent is evaporated off. A mixture of cis and trans isomer is obtained, which is separated by flash chromatography, eluting with a 98/2/0.2 methylene chloride/methanol/NH$_4$OH mixture. The compound of the title is obtained as a white solid (R.f. lower compared to the cis isomer).

PREPARATION 11 trans-1-(4-N-Benzylaminocyclohexyl)benzonitrile

A mixture of cis and trans isomer is obtained by carrying out the procedure as described in Preparation 10, but using 4-(4-cyanophenyl)cyclohexanone instead of 4-phenylcyclohexanone, which mixture is separated by flash chromatography, eluting with a 9/1 chloroform/methanol mixture. The compound of the title is obtained as a white solid (R.f. lower compared to the cis isomer—semi-solid).

M.p. 117-119° C.

PREPARATION 12 trans-4-(4-N-Benzylaminocyclohexyl)benzamide 1.1 g (3.90 mmol) of the product of Preparation 11, 1 ml of 20% NaOH and 1 ml of 30% H$_2$O$_2$ are mixed. The mixture is stirred at room temperature for 15 minutes and then 5 ml of methanol are slowly added. A yellow solution is obtained which is vigorously stirred for 5 hours. The white solution thus obtained is diluted with 50 ml of water and the mixture is extracted with methylene chloride. The organic phase is dried and the solvent is evaporated off. The product is treated in diethyl ether. The product of the title is obtained.

M.p. 207-210° C.

PREPARATION 13

4-Methoxy-3-[(N-methylsulphonyl-N-tert-butoxycarbonyl)amino]-1-((2S)2,3-epoxypropoxy)benzene The compound of the title is obtained by carrying out the procedure as described in Preparation 4 (ii), (iii) and (iv), but using 4-methoxy-3-(methylsulphonylamino)phenyl acetate instead of 4-benzyloxy-3-(phenylsulphonylamino)phenyl acetate.

M.p. 133-135° C.

PREPARATION 14 trans-Ethyl 1-(4-N-benzylaminocyclohexyl)benzoate

A mixture of cis and trans isomer is obtained by carrying out the procedure as described in Preparation 10, but using 4-(4-ethoxycarbonylphenyl)cyclohexanone instead of 4-phenylcyclohexanone, which mixture is separated by flash chromatography, eluting with a 7/3 cyclohexane/ethyl acetate mixture. The compound of the title is obtained as a white solid (R.f. lower compared to the cis isomer, which is semi-solid).

M.p. 74-76° C.

PREPARATION 15

3-(Methylsulphonyl)-5-[(2S)-oxyranylmethoxy]-1,3-benzoxazol-2(3H)-one (i) 5-Methylcarbonyl-1,3-benzoxazol-2(3H)-one 7.8 ml of triethylamine and 2.75 g (0.0093 mol) of triphosgene are added to a mixture of 4.2 g (0.0277 mol) of 2-amino-4-methylcarbonylphenol in 100 ml of THF, at 0° C. The mixture is stirred at room temperature for 1 hour, poured into 100 ml of a 0.5N HCl solution and extracted with ethyl acetate, the organic phase is dried and the solvent is evaporated off. The compound of the title is obtained.

M.p. 231-234° C. (ii) 3-Methylsulphonyl-5-methylcarbonyl-1,3-benzoxazol-2 (3H)-one 1.7 g (0.0096 mol) of the product of the previous step is dissolved in 60 ml of anhydrous methylene chloride and 1.35 ml of triethylamine are added to this, followed, at 0° C., by 0.75 ml (0.0096 mol) of mesyl chloride under a nitrogen stream. The mixture is stirred at room temperature overnight. It is poured into water, the organic phase is dried and the solvent is evaporated off. The product is purified by chromatography, eluting with a 6/4 cyclohexane/ethyl acetate mixture. The compound of the title is obtained.

M.p. 140-143° C.

(iii) 3-Methylsulphonyl-1,3-benzoxazol-2(3H)-on-5-yl acetate

A mixture of 3.3 g (0.013 mol) of the product of the previous step and 16.1 g (0.065 mol) of 3-chloroperbenzoic acid (MCPBA) in 200 ml of methylene chloride is refluxed for 48 hours. The mixture is cooled, and then washed with a 20% $Na_2S_2O_5$ solution, followed by a saturated sodium bicarbonate solution, a sodium iodide solution and water. The organic phase is dried and the solvent is evaporated off. The product is purified by chromatography, eluting with a 75/25 cyclohexane/ethyl acetate mixture. The compound of the title is obtained as a white solid.

M.p. 159-162° C.

(iv) 5-Hydroxy-3-(methylsulphonyl)-1,3-benzoxazol-2 (3H)-one 735 mg (2.71 mmol) of the product of the previous step are dissolved in 50 ml of ethanol and 2.06 g (10.84 mmol) of p-toluenesulphonic acid are added to this. The mixture is stirred for 3 hours and then diluted with 100 ml of methylene chloride. The mixture is washed with a sodium bicarbonate solution, the organic phase is dried and the solvent is evaporated off. The compound of the title is obtained.

M.p. 129-130° C.

(v) 3-(Methylsulphonyl)-5-[(2S)-oxyranylmethoxy]-1,3-benzoxazol-2(3H)-one

The compound of the title is obtained by carrying out the procedure as described in Preparation 4 (iv), but using the product of the previous step instead of 4-benzyloxy-3-(N-tert-butoxycarbonyl-N-phenylsulphonylamino)phenol.

M.p. 100-102° C.

PREPARATION 16

5-(Methylsulphonyl)-7-[(2S)-oxyranylmethoxy]-2,3,4,5-tetrahydro-1,5-benzoxazepine (i) 7-Hydroxy-5-(methylsulphonyl)-2,3,4,5-tetrahydro-1,5-benzoxazepine 0.568 g (2.32 mmol) of 4-hydroxy-3-methylsulphonylaminophenyl acetate (obtained by hydrogenation of the corresponding benzyloxy derivative), 0.672 g of potassium carbonate in 20 ml of DMF are mixed under a nitrogen stream, and 0.259 ml of 1,3-dibromopropane is then added to this. The mixture is stirred at room temperature overnight. Water is added and the mixture is extracted with ethyl acetate. The organic phase is dried and the solvent is evaporated off. A purple oil is obtained which is taken up in 8 ml of methanol and 1.88 ml of 1M NaOH. Water is then added, followed by picric acid until a neutral pH is obtained. The methanol is evaporated off and the remaining mixture is extracted with ethyl acetate. The organic phase is dried and the solvent is evaporated off. The product is purified by chromatography, eluting with a 7/3 cyclohexane/ethyl acetate mixture. The compound of the title is obtained.

(ii) 5-(Methylsulphonyl)-7-[(2S)-oxyranylmethoxy]-2,3,4, 5-tetrahydro1,5-benzoxazepine The compound of the title is obtained as a white solid by carrying out the procedure as described in Preparation 4 (iv), but using the product of the previous step instead of the product of step 4 (iii).

PREPARATION 17

4-(2-Trimethylsilylethoxymethoxy)-3-chloro-1-((2S) 2,3-epoxypropoxy)phenol (i) 3-Chloro-4-(2-trimethylsilylethoxymethoxy)benzaldehyde 5 g (31.93 mmol) of 5-chloro-4-hydroxybenzaldehyde are dissolved in 300 ml of methylene chloride and 6.7 ml (38.3 mmol) of N,N-diisopropyl-N-ethylamine and 5.9 ml (33.52 mmol) of 2-trimethylsilylethoxymethyl chloride (SEMCl) are added to this at 0° C. The mixture is allowed to return to room temperature and stirred overnight. Water is then added and the mixture is extracted with methylene chloride. The organic phase is dried and the solvent is evaporated off. The product of the title is obtained, which is purified by chromatography on a silica gel column, eluting with a 95/5 and then 9/1 heptane/ethyl acetate mixture.

(ii) 3-Chloro-4-(2-trimethylsilylethoxymethoxy)phenol 10.6 g of meta-chloroperbenzoic acid at 70% are added to a mixture of 7.5 g (26.14 mmol) of the product of the previous step in 260 ml of methylene chloride at 0° C. The mixture is allowed to return to room temperature and stirred overnight. A sodium bicarbonate solution is then added and the mixture is extracted with methylene chloride. The organic phase is dried and the solvent is evaporated off. The product of the title is obtained, which is purified by chromatography on a silica gel column, eluting with a 9/1 cyclohexane/ethyl acetate mixture.

(iii) 4-(2-Trimethylsilylethoxymethoxy)-3-chloro-1-((2S)2, 3-epoxypropoxy)benzene The compound of the title is obtained as a white solid by carrying out the procedure as described in Preparation 4 (iv), but using the product of the previous step instead of the product step 4 (iii).

PREPARATION 18 trans-N-[4-(4-Aminocyclohexyl)benzoyl]pyrrolidine

The compound of the title is obtained by carrying out the procedure as described in Preparation 8 (iii) and (iv), but using pyrrolidine instead of diethylamine.

PREPARATION 19 cis- and trans-4-[4-(4,4-Dimethyl-4,5-dihydro-1,3-oxazol-2-yl)phenyl]cyclohexanamine The cis and trans mixture of the product of the title is obtained in a ratio of approximately 3/7, by carrying out the procedure as described in Preparation 3, but using 4-[4-(4,4-dimethyl-4,5-dihydro-1,3-oxazol-2-yl)phenyl]cyclohexanone, and without adding to the mixture the ethanol saturated with hydrochloric acid. These isomers are separated by HPLC under the following conditions:

Column: CHROMOLITH RP 18 Eluent: $KH_2PO_4$ (0.05M), pH 3.5/acetonitrile=80/20 Flow rate: 1 ml/min. λ: 254 nm TRR1: 1.00 (trans isomer) TRR2: 1.08 (cis isomer)

PREPARATION 20 trans-1-(4-N-Benzylaminocyclohexyl)-4-ethylcarbonylbenzene (i) trans-1-(4-(N-Benzylamino-N-tert-butoxycarbonyl)cyclohexyl)benzonitrile 380 mg (1.3 mmol) of the product of Preparation 11 are dissolved in 4.5 ml of THF and 343 mg (1.5 mmol) of di-tert-butyl dicarbonate and 0.220 ml of triethylamine are added to this. The mixture is stirred at room temperature overnight, 40 ml of water are added, the aqueous phase is extracted with ethyl acetate, the organic phase is dried and the solvent is evaporated off. The product of the title is thus obtained.

(ii) trans-1-(4-N-Benzylamino-N-tert-butoxycarbonyl)cyclohexyl-4-ethylcarbonylbenzene 1.06 g (2.72 mmol) of the product of the previous step are dissolved in 40 ml of anhydrous toluene and 5.4 ml (5.43 mmol) of ethylmagnesium bromide (EtMgBr) at the temperature of 0-5° C. are added to this under a nitrogen stream. The mixture is stirred at room temperature overnight, 50 ml of water are added, the aqueous phase is extracted with ethyl acetate, the organic phase is dried and the solvent is evaporated off. The product of the title is thus obtained.

(iii) trans-1-(4-N-Benzylaminocyclohexyl)-4-ethylcarbonylbenzene

A mixture of 1.17 g (2.77 mol) of the product of the previous step and 30.7 ml of a solution of trifluoroacetic acid in methylene chloride at 15% is stirred at room temperature overnight. Ethyl acetate is then added and the mixture is washed with a sodium bicarbonate solution. The organic phase is dried and the solvent is evaporated off. The product of the title is thus obtained.

PREPARATION 21 trans-tert-Butyl 1-(4-N-benzylaminocyclohexyl)benzoate

The product of the title is prepared by trans-esterification of the product of Preparation 14, according to the method described in J.O.C., 1997, 62:8240.

EXAMPLE 1 trans-Ethyl 4-[4-((2S)-3-(4-benzyloxy-3-(methylsulphonylamino)phenoxy)-2-hydroxypropylamino)cyclohexyl]benzoate Formula (I): A=(a); $R_1$=Bn; R=—$NHSO_2$—Me; n,m=0; $R_3$=4-COOEt A mixture of 818 mg of 4-benzyloxy-3-(N-tert-butoxycarbonyl-N-methylsulphonylamino)-1-((2S)2,3-epoxypropoxy)benzene (1.82 mmol) and 450 mg of the "trans" product obtained according to Preparation 3 in the form of a base (1.82 mmol) in 15 ml of absolute ethanol is refluxed for 16 hours. The mixture is cooled, 3 ml of a solution of ethanol saturated with hydrochloric acid are added to this and the mixture is heated at 50° C. for 6 hours. The solvent is evaporated off and the residue is taken up with a mixture of 50 ml of a saturated sodium bicarbonate solution and 50 ml of ethyl acetate. The organic phase is washed with a saturated aqueous NaCl solution. The organic phase is dried and, after filtration, the solvent is evaporated off under reduced pressure. The crude product is purified by chromatography on a silica gel column, eluting with a 95/5/0.5 methylene chloride/methanol/$NH_4OH$ mixture. The compound of the title is obtained in the form of a white solid.

M.p. 132-134° C.

EXAMPLE 2 trans-Ethyl 4-[4-((2S)-2-hydroxy-3-(4-hydroxy-3-(methylsulphonylamino)phenoxy)propylamino)cyclohexyl]benzoate hydrochlorate Formula (I): A=(a); $R_1$=H; R=—$NHSO_2$—Me; n,m=0; $R_3$=4-COOEt A solution of 500 mg of the product of Example 1 (838 mmol) in 25 ml of a mixture of ethanol and THF is stirred at room temperature in a hydrogen atmosphere for 7 hours, in the presence of 400 mg of Pd/C at 10%. The catalyst is filtered, the solvent is evaporated off under reduced pressure and the crude product is purified by chromatography on a silica gel column, eluting with a 95/5/0.5 methylene chloride/methanol/$NH_4OH$ mixture. The compound of the title is obtained in the form of a base. The hydrochlorate of this base is obtained by treating it with a solution of hydrochloric acid in ethanol.

M.p. 183-185° C.

The product thus obtained is subsequently purified by crystallization in isopropanol.

M.p. 188-190° C.

EXAMPLE 3 cis-Ethyl 4-[4-((2S)-2-hydroxy-3-(4-hydroxy-3-(methylsulphonylamino)phenoxy)propylamino)cyclohexyl]benzoate Formula (I): A=(a); $R_1$=H; R=—$NHSO_2$—Me; n,m=0; $R_3$=4-COOEt 3a. cis-Ethyl 4-[4-((2S)-3-(4-benzyloxy-3-(N-methylsulphonylamino)phenoxy)-2-hydroxypropylamino)cyclohexyl]benzoate The compound of the title is obtained as a vitreous white solid, by carrying out the procedure as described in Example 1, but using the cis product of Preparation 3.

3b. cis-Ethyl 4-[4-((2S)-2-hydroxy-3-(4-hydroxy-3-(methylsulphonylamino)phenoxy)propylamino)cyclohexyl]benzoate and its hydrochlorate The compound of the title is obtained by carrying out the procedure as described in Example 2, but using the product of the previous step instead of the product of Example 1.

M.p. 135-138° C. (hydrochlorate)

EXAMPLE 4 trans-Ethyl 4-[4-((2S)-2-hydroxy-3-(4-hydroxy-3-(phenylsulphonylamino)phenoxy)propylamino)cyclohexyl]benzoate and its hydrochlorate Formula (I): A=(a); $R_1$=H; R=—$NHSO_2$—Ph; n,m=0; $R_3$=4-COOEt 4a. trans-Ethyl 4-[4-((2S)-2-hydroxy-3-(4-benzyloxy-3-(phenylsulphonylamino)phenoxy)propylamino)cyclohexyl]benzoate The compound of the title is obtained by carrying out the procedure as described in Example 1, but using the epoxide of Preparation 4.

M.p. 113-115° C.

4b. trans-Ethyl 4-[4-((2S)-2-hydroxy-3-(4-hydroxy-3-(phenylsulphonylamino)phenoxy)propylamino)cyclohexyl]benzoate and its hydrochlorate The compound of the title is obtained by carrying out the procedure as described in Example 2, but using the product of Example 4a instead of the product of Example 1.

M.p. 172-174° C. (hydrochlorate).

EXAMPLE 5 trans-Ethyl 4-[4-((2S)-2-hydroxy-3-(4-hydroxy-3-(n-butylsulphonylamino)phenoxy)propylamino)cyclohexyl]benzoate and its hydrochlorate Formula (I): A=(a); $R_1$=H; R=—NHSO$_2$—nBu; n,m=0; $R_3$=4-COOEt 5a. trans-Ethyl 4-[4-((2S)-2-hydroxy-3-(4-benzyloxy-3-(n-butylsulphonylamino)phenoxy)propylamino)cyclohexyl]benzoate The compound of the title is obtained by carrying out the procedure as described in Example 1, but using the epoxide of Preparation 5.

M.p. 108-110° C.

5b. trans-Ethyl 4-[4-((2S)-2-hydroxy-3-(4-hydroxy-3-(n-butylsulphonylamino)phenoxy)propylamino)cyclohexyl]benzoate and its hydrochlorate The compound of the title is obtained by carrying out the procedure as described in Example 2, but using the product of Example 5a instead of the product of Example 1.

M.p. 149-151° C. (hydrochlorate).

EXAMPLE 6 trans-Ethyl 4-[4-((2S)-2-hydroxy-3-(4-hydroxy-3-(benzylsulphonylamino)phenoxy)propylamino)cyclohexyl]benzoate and its hydrochlorate Formula (I): A=(a); $R_1$=H; R=—NHSO$_2$—Bn; n,m=0; $R_3$=4-COOEt 6a. trans-Ethyl 4-[4-((2S)-2-hydroxy-3-(4-benzyloxy-3-(benzylsulphonylamino)phenoxy)propylamino)cyclohexyl]benzoate The compound of the title is obtained in the form of a vitreous white solid, by carrying out the procedure as described in Example 1, but using the epoxide of Preparation 6.

6b. trans-Ethyl 4-[4-((2S)-2-hydroxy-3-(4-hydroxy-3-(benzylsulphonylamino)phenoxy)propylamino)cyclohexyl]benzoate and its hydrochlorate 430 mg of the product of the previous step are dissolved in 7.5 ml of trifluoroacetic acid and the mixture is heated at 60° C. for 3 hours. The solvent is evaporated off under reduced pressure and the residue is taken up in a mixture of aqueous sodium bicarbonate and ethyl acetate. 300 mg of potassium carbonate are added and the two phases are separated. The organic phase is washed with a sodium chloride solution, it is dried over sodium sulphate and the solvent is evaporated off under reduced pressure. The residue is purified by flash chromatography on a silica gel column, eluting with a 95/5/05 CH$_2$Cl$_2$/MeOH/NH$_3$ mixture. The compound of the title is thus obtained. Its hydrochlorate is prepared using a solution of hydrochloric acid in ethyl acetate.

M.p. 170-172° C. (hydrochlorate).

EXAMPLE 7 trans-Ethyl 4-[4-((2S)-2-hydroxy-3-(4-hydroxy-3-(methylsulphonyl)phenoxy)propylamino)cyclohexyl]benzoate Formula (I): A=(a); $R_1$=H; R=—SO$_2$—Me; n,m=0; $R_3$=4-COOEt 7a. trans-Ethyl 4-[4-((2S)-2-hydroxy-3-(4-benzyloxy-3-(methylsulphonyl)phenoxy)propylamino)cyclohexyl]benzoate The compound of the title is obtained by carrying out the procedure as described in Example 1, but using 4-benzyloxy-3-methylsulphonyl-1-((2S)2,3-epoxypropoxy)benzene (described in WO 99/65895), and without adding to the mixture the solution of hydrochloric acid in ethanol.

M.p. 142-144° C.

7b. trans-Ethyl 4-[4-((2S)-2-hydroxy-3-(4-hydroxy-3-(methylsulphonyl)phenoxy)propylamino)cyclohexyl]benzoate The compound of the title is obtained by carrying out the procedure as described in Example 6b, but using the product of Example 7a instead of the product of Example 6a.

M.p. 173-175° C.

EXAMPLE 8 trans-N-[5-[[((2S)-3-((4-(4-(4,4-Dimethyl-4,5-dihydro-1,3-oxazol-2-yl)phenyl)cyclohexyl)amino)-2-hydroxypropyl]oxy]-2-hydroxyphenyl]methanesulphonamide Formula (I): A=(a); $R_1$=H; R=—NHSO$_2$—Me; n,m=0; $R_3$=4-Ox 8a. trans-N-[5-[[((2S)-3-((4-(4-(4,4-Dimethyl-4,5-dihydro-1,3-oxazol-2-yl)-phenyl)cyclohexyl)amino)-2-hydroxypropyl]oxy]-2-benzyloxyphenyl]-N-benzyl-N-methanesulphonamide The compound of the title, free of cis isomer, is obtained as a vitreous solid by carrying out the procedure as described in Example 1, but without adding to the mixture the ethanol solution saturated with HCl, and using the epoxide of Preparation 7 and the product of Preparation 19.

8b. trans-N-[5-[[((2S)-3-((4-(4-(4,4-Dimethyl-4,5-dihydro-1,3-oxazol-2-yl)phenyl)cyclohexyl)amino)-2-hydroxypropyl]oxy]-2-hydroxyphenyl]methanesulphonamide The compound of the title is obtained by carrying out the procedure as described in Example 2, but using the product of Example 8a instead of the product of Example 1.

M.p. 75-78° C.

EXAMPLE 9 trans-4-[4-((2S)-2-Hydroxy-3-(4-hydroxy-3-(methylsulphonylamino)phenoxy)propylamino)cyclohexyl]-N,N-diethylbenzamide Formula (I): A=(a); $R_1$=H; R=—NHSO$_2$—Me; n,m=0; $R_3$=4-CONEt$_2$ 9a. trans-4-[4-((2S)-2-Hydroxy-3-(4-benzyloxy-3-(methylsulphonylamino)phenoxy)propylamino)cyclohexyl]-N,N-diethylbenzamide The compound of the title is obtained by carrying out the procedure as described in Example 1, but using the product of Preparation 8 instead of the product of Preparation 3.

M.p. 48-50° C.

9b. trans-4-[4-((2S)-2-Hydroxy-3-(4-hydroxy-3-(methylsulphonylamino)phenoxy)propylamino)cyclohexyl]-N,N-diethylbenzamide The compound of the title is obtained by carrying out the procedure as described in Example 2, but using the product of Example 9a instead of the product of Example 1.

M.p. 69-72° C.

EXAMPLE 10 trans-4-[4-((2S)-2-Hydroxy-3-(4-hydroxy-3-(methylsulphonylamino)phenoxy)propylamino)cyclohexyl]-N-n-butylbenzamide Formula (I): A=(a); $R_1$=H; R=—$NHSO_2$—Me; n,m=0; $R_3$=4-CONHBu 10a. trans-4-[4-((2S)-2-Hydroxy-3-(4-benzyloxy-3-(methylsulphonylamino)phenoxy)propylamino)cyclohexyl]-N-n-butylbenzamide The compound of the title is obtained by carrying out the procedure as described in Example 1, but using the product of Preparation 9 instead of the product of Preparation 3.

M.p. 138-140° C.

10b. trans-4-[4-((2S)-2-Hydroxy-3-(4-hydroxy-3-(methylsulphonylamino)phenoxy)propylamino)cyclohexyl]-N-n-butylbenzamide The compound of the title is obtained by carrying out the procedure as described in Example 2, but using the product of Example 10a instead of the product of Example 1.

M.p. 144-146° C.

EXAMPLE 11 trans-4-[4-((2S)-2-Hydroxy-3-(4-hydroxy-3-(methylsulphonylamino)phenoxy)propylamino)cyclohexyl]benzene Formula (I): A=(a); $R_1$=H; R=—$NHSO_2$—Me; n,m=0; $R_3$=H 11a. trans-4-[4-((2S)-2-Hydroxy-3-(4-benzyloxy-3-(methylsulphonylamino)phenoxy)propyl-(N-benzyl)amino)cyclohexyl]benzene The compound of the title is obtained by carrying out the procedure as described in Example 1, but using the product of Preparation 10 instead of the product of Preparation 3, and eluting with 8/2 cyclohexane/ethyl acetate.

11b. trans-4-[4-((2S)-2-Hydroxy-3-(4-hydroxy-3-(methylsulphonylamino)phenoxy)propylamino)cyclohexyl]benzene The compound of the title is obtained by carrying out the procedure as described in Example 2, but using the product of Example 11a instead of the product of Example 1.

M.p. 172-175° C.

EXAMPLE 12 trans-4-[4-((2S)-2-Hydroxy-3-(4-hydroxy-3-(methylsulphonylamino)phenoxy)propylamino)cyclohexyl]benzoic acid Formula (I): A=(a); $R_1$=H; R=—$NHSO_2$—Me; n,m=0; $R_3$=4-COOH A solution of 0.1167 g of the product of Example 2 (base) (0.33 mmol) in a mixture of 1.6 mL of methanol and of 1.6 mL of a 1N aqueous sodium hydroxide solution is stirred for 4 hours. The acidified reaction medium is then acidified by adding 1.6 mL of a 1N aqueous hydrochloric acid solution, and then the mixture is diluted with methanol. The product of the title is obtained (0.08 g, yield=5%) in the form of trifluoroacetate, after purification on preparative HPLC/MS and evaporation of the solvents.

Apparatus: two Shimatzu LC8 pumps coupled to a PE Sciex API 100 mass spectrometer. An SCL-10A controller. A Gilson 215 injector-fraction collector.

Stationary phase: Xterra MS C18, 50×30 mm, 5 μm
Mobile phase:
Eluent A: 95/5 $H_2O$/MeOH+0.05% $CF_3COOH$
Eluent B: 5/95 $H_2O$/MeOH+0.05% $CF_3COOH$
Flow rate: 30 mL/min
Elution gradient:

| t (in min) | % A | % B |
|---|---|---|
| 0 | 90 | 10 |
| 3 | 90 | 10 |
| 15 | 10 | 90 |
| 17 | 10 | 90 |

TR=8.17 min, [M+H$^+$]=479.3.

The purified product was analysed by HPLC under the following conditions.

Apparatus: two Shimatzu LC8 pumps coupled to an SPD10-A UV-detector and a PE Sciex API 100 mass spectrometer. An SCL-10A controller. A Gilson 215 injector-fraction collector.

Stationary phase: Xterra MS C18, 50×4.6 mm, 5 μm.
Mobile phase:
Eluent A: 95/5 $H_2O$/MeOH+0.05% $CF_3COOH$
Eluent B: 5/95 $H_2O$/MeOH+0.05% $CF_3COOH$
Flow rate: 3 mL/min
Elution gradient:

| t (in min) | % A | % B |
|---|---|---|
| 0 | 90 | 10 |
| 1 | 90 | 10 |
| 9 | 10 | 90 |
| 10 | 10 | 90 |

TR=4.79 min, [M+H$^+$]=479.3.

EXAMPLE 13 trans-4-[4-((2S)-2-Hydroxy-3-(4-hydroxy-3-(methylsulphonylamino)phenoxy)propylamino)cyclohexyl]benzonitrile Formula (I): A=(a); $R_1$=H; R=—$NHSO_2$—Me; n,m=0; $R_3$=4-CN 13a. trans-4-[4-((2S)-2-Hydroxy-3-(4-benzyloxy-3-(methylsulphonylamino)phenoxy)propyl-(N-benzyl)amino)cyclohexyl]benzonitrile The compound of the title is obtained by carrying out the procedure as described in Example 1, but using the product of Preparation 11 instead of the product of Preparation 3, and eluting with 9/1 methylene chloride/methanol.

13b. trans-4-[4-((2S)-2-Hydroxy-3-(4-hydroxy-3-(methylsulphonylamino)phenoxy)propylamino)cyclohexyl]benzonitrile The compound of the title is obtained by carrying out the procedure as described in Example 2, but using the product of Example 13a instead of the product of Example 1, and using PdOH$_2$/C instead of Pd/C.

¹H NMR (CDCl₃+D₂O; ppm); 1.13-1.66 (4H; m); 1.77-2.00 (2H; m); 2.00-2.19 (2H; m); 2.35-3.09 (4H; m); 2.89 (3H; s); 3.70-3.93 (2H; m); 3.96-4.16 (1H; m); 6.42 (1H; dd; 9 Hz; 2 Hz); 6.72 (1H; d; 8 Hz); 6.92 (1H; d; 2 Hz); IR (KBr; cm⁻¹): 3430; 2227; 1324; 1151

EXAMPLE 14 trans-4-[4-((2S)-2-Hydroxy-3-(4-hydroxy-3-(methylsulphonylaminophenoxy)propylamino)cyclohexyl]benzamide Formula (I): A=(a); R₁=H; R=—NHSO₂—Me; n,m=0; R₃=4-CONH₂

14a. trans-4-[4-((2S)-2-Hydroxy-3-(4-benzyloxy-3-(methylsulphonylamino)phenoxy)propyl-(N-benzyl)amino)cyclohexyl]benzamide The compound of the title is obtained by carrying out the procedure as described in Example 1, but using the production of Preparation 12 instead of the product of Preparation 3, and eluting with 2/1 cyclohexane/ethyl acetate.

14b. trans-4-[4-((2S)-2-Hydroxy-3-(4-hydroxy-3-(methylsulphonylamino)phenoxy)propylamino)cyclohexyl]benzamide The compound of the title is obtained by carrying out the procedure as described in Example 2, but using the product of Example 14a instead of the product of Example 1.

M.p. 79-81° C.

EXAMPLE 15 trans-Ethyl 4-[4-((2S)-2-hydroxy-3-(4-methoxy-3-(methylsulphonylamino)phenoxy)propylamino)cyclohexyl]benzoate Formula (I): A=(a); R₁=Me; R=—NHSO₂—Me; n,m=0; R₃=4-COOEt 15a. trans-Ethyl 4-[4-((2S)-2-hydroxy-3-(4-methoxy-3-(methylsulphonylamino)phenoxy)propyl-(N-benzyl)amino)cyclohexyl]benzoate The compound of the title is obtained as a vitreous solid by carrying out the procedure as described in Example 1, but using the product of Preparation 13 and the product of Preparation 14, and eluting with 1/1 cyclohexane/ethyl acetate.

15b. trans-Ethyl 4-[4-((2S)-2-hydroxy-3-(4-methoxy-3-(methylsulphonylamino)phenoxy)propylamino)cyclohexyl]benzoate The compound of the title is obtained by carrying out the procedure as described in Example 2, but using the product of Example 15a instead the product of Example 1.

M.p. 144-146° C.

EXAMPLE 16 trans-Ethyl 4-[4-((2S)-2-hydroxy-3-[(3-(methylsulphonyl)-2-oxo-2,3-dihydro-1,3-benzoxazol-5-yl]oxy)propyl)amino)cyclohexyl]benzoate Formula (I): A=(b); X=CO; R₂=—SO₂Me; n,m=0; R₃=4-COOEt 16a. trans-Ethyl 4-[4-(benzyl-((2S)-2-hydroxy-3-[(3-(methylsulphonyl)-2-oxo-2,3-dihydro-1,3-benzoxazol-5-yl]oxy)propyl)amino)cyclohexyl]benzoate The compound of the title is obtained as a vitreous solid by carrying out the procedure as described in Example 1, but using the epoxide of Preparation 15 and the product of Preparation 14, but without adding to the mixture the solution of ethanol saturated with HCl, and eluting with 1/1 cyclohexane/ethyl acetate.

16b. trans-Ethyl 4-[4-(((2S)-2-hydroxy-3-[(3-(methylsulphonyl)-2-oxo-2,3-dihydro-1,3-benzoxazol-5-yl]-oxy)propyl)amino)cyclohexyl]benzoate The compound of the title is obtained by carrying out the procedure as described in Example 2, but using the product of Example 16a instead of the product of Example 1.

M.p. 146-148° C.

EXAMPLE 17 trans-Ethyl 4-[4-((2S)-2-hydroxy-3-((5-methylsulphonyl-2,3,4,5-tetrahydro-1,5-benzoxazepin-7-yl)oxy)propylamino)cyclohexyl]benzoate and its hydrochlorate Formula (I): A=(b); X=CH₂CH₂CH₂; R₂=—SO₂Me; n,m=0; R₃=4-COOEt 17a. trans-Ethyl 4-[4-((2S)-2-hydroxy-3-((5-methylsulphonyl-2,3,4,5-tetrahydro-1,5-benzoxazepin-7-yl)oxy)propyl-(N-benzyl)amino)cyclohexyl]benzoate The compound of the title is obtained by carrying out the procedure as described in Example 1, but using the epoxide of Preparation 16 and the product of Preparation 14, and without adding to the mixture the solution of ethanol saturated with HCl, and eluting with 98/2 methylene chloride/ethanol.

17b. trans-Ethyl 4-[4-((2S)-2-hydroxy-3-((5-methylsulphonyl-2,3,4,5-tetrahydro-1,5-benzoxazepin-7-yl)oxy)propylamino)cyclohexyl]benzoate and its hydrochlorate The compound of the title is obtained by carrying out the procedure as described in Example 2, but using the product of Example 17a instead of the product of Example 1.

M.p. 170-173° C. (hydrochlorate).

EXAMPLE 18 trans-Ethyl 4-[4-((2S)-2-hydroxy-3-(4-hydroxy-3-chlorophenoxy)propylamino)cyclohexyl]benzoate and its hydrochlorate Formula (I): A=(a); R₁=H; R=Cl; n,m=0; R₃=4-COOEt 18a. trans-Ethyl 4-[4-((2S)-2-hydroxy-3-(4-(2-trimethylsilylethoxymethoxy)-3-chlorophenoxy)propylamino)cyclohexyl]benzoate The compound of the title is obtained by carrying out the procedure as described in Example 1, but using the epoxide of Preparation 17, and without adding to the mixture the solution of hydrochloric acid.

18b. trans-Ethyl 4-[4-((2S)-2-hydroxy-3-(4-hydroxy-3-chlorophenoxy)propylamino)cyclohexyl]benzoate and its hydrochlorate A mixture of 0.34 g (0.588 mmol) of the product of the previous step, 0.46 g (1.76 mmol) of tetrabutylammonium fluoride and 0.2 ml of hexamethylphosphoramide in 5 ml of THF is refluxed overnight. The solvent is evaporated off, the residue is taken up with ethyl acetate and washed with water, the organic phase is dried and the solvent is evaporated off under reduced pressure. The crude product is purified by chromatography on a silica gel column, eluting with a 95/5 and then a 90/10 CH₂Cl₂/EtOH mixture. The compound of the title is obtained. The hydrochlorate of the base is obtained by treating it with a solution of hydrochloric acid in ethyl ether.

M.p. 223-225° C.

EXAMPLE 19 trans-N-[4-[4-((2S)-2-Hydroxy-3-(4-hydroxy-3-methylsulphonylaminophenoxy)propylamino)cyclohexyl]benzoyl]pyrrolidine Formula (I): A=(a); $R_1$=H; R=—$NHSO_2$—Me; n,m=0; $R_3$=4-CO-pyrrolidine 19a. trans-N-[4-[4-((2S)-2-Hydroxy-3-(4-benzyloxy-3-methylsulphonylaminophenoxy)propylamino)cyclohexyl]benzoyl]pyrrolidine The compound of the title is obtained by carrying out the procedure as described in Example 1, but using the product of Preparation 18 instead of the product of Preparation 3.

19b. trans-N-[4-[4-((2S)-2-Hydroxy-3-(4-hydroxy-3-methylsulphonylaminophenoxy)propylamino)cyclohexyl]benzoyl]pyrrolidine The compound of the title is obtained by carrying out the procedure as described in Example 2, but using the product of previous step instead of the product of Example 1.

$[\alpha]_D$=−1.6° (c=0.264, EtOH).

EXAMPLE 20 trans-Ethyl 4-[4-((2S)-2-hydroxy-3-(4-hydroxyphenoxy)propylamino)cyclohexyl]benzoate Formula (I): A=(a); $R_1$=H; R=—H; n,m=0; $R_3$=4-COOEt The compound of the title is obtained by carrying out the procedure as described in Example 1, but using 4-benzyloxy-1-((2S)2,3-epoxypropoxy)benzene and without adding to the mixture the solution of hydrochloric acid, and then according to Example 2.

M.p. 146° C.

EXAMPLE 21 trans-4-[4-((2S)-2-Hydroxy-3-(4-hydroxy-3-(methylsulphonylamino)phenoxy)propylamino)cyclohexyl]-1-ethylcarbonylbenzene Formula (I): A=(a); $R_1$=H; R=—$NHSO_2$—Me; n,m=0; $R_3$=4-COEt The compound of the title is obtained in the form of a light brown solid, by carrying out the procedure as described in Example 1, but using the product of Preparation 20 instead of the product of Preparation 3 and eluting with 7/3 cyclohexane/ethyl acetate mixture, and then according to Example 2, but using $PdOH_2$/C instead of Pd/C.

$^1$H NMR (DMSO-D6+$D_2$O 313K; ppm); 1.08 (3H; t; 7 Hz); 1.37-1.68 (4H; m); 1.73-2.00 (2H; m); 2.05-2.29 (2H; m); 2.42-2.70 (2H; m); 2.82-3.21 (4H; m); 2.94 (3H; s); 3.80-3.99 (2H; m); 4.03-4.22 (1H; m); 6.53-6.74 (1H; m); 7.74-6.96 (2H; m); 7.30-7.54 (2H; m); 7.79-8.02 (2H; m).

EXAMPLE 22 trans-tert-Butyl 4-[4-((2S)-2-hydroxy-3-(4-hydroxy-3-(methylsulphonylamino)phenoxy)propylamino)cyclohexyl]benzoate Formula (I): A=(a); $R_1$=H; R=—$NHSO_2$—Me; n,m=0; $R_3$=4-COO-tBu A mixture of 782.4 mg (1.78 mmol) of the epoxide of Preparation 7 and 650 mg of the product of Preparation 21 (1.78 mmol) in 9 ml of tert-butyl alcohol is refluxed for 16 hours. The solvent is evaporated off under reduced pressure, and the product is purified by chromatography on a silica gel column, eluting with 1/1 methylene chloride/ethyl acetate. A solution of 880 mg of the product thus prepared in 30 ml of THF is hydrogenated at room temperature for 7 hours in the presence of 264 mg Pd/C at 10%. The catalyst is filtered, the solvent is evaporated off under reduced pressure and the crude product is purified by chromatography on a silica gel column, eluting with THF. The compound of the title is obtained, which is purified by treatment with n-pentane.

$^1$H NMR (DMSO-D6+$D_2$O 313K; ppm); 1.10-1.28 (2H; m); 1.38-1.65 (2H; m); 1.53 (9H; s); 1.70-1.1.90 (2H; m); 1.90-2.09 (2H; m); 2.41-2.71 (3H; m); 2.71-2.83 (1H; m); 2.94 (3H; s); 3.72-3.95 (3H; m); 6.61 (1H; dd; 9 Hz; 3 Hz); 6.78 (1H; dd; 9 Hz); 6.82 (1H; dd; 3 Hz); 7.28-7.37 (2H; m); 7.75-7.85 (2H; m).

EXAMPLE 23 trans-4-[4-(((2S)-2-Hydroxy-3-[3-(methylsulphonyl)-2-oxo-2,3-dihydro-1,3-benzoxazol-5-yl]-oxy)propylamino)cyclohexyl]benzamide Formula (I): A=(b); X=CO; $R_2$=—$SO_2$Me; n,m=0; $R_3$=4-$CONH_2$ The compound of the title is obtained by carrying out the procedure as described in Example 1, but using the epoxide of Preparation 15 and the product of Preparation 12, and without adding to the mixture the solution of ethanol saturated with HCl, and then as described in Example 2.

$^1$H NMR (DMSO-D6; 313K; ppm); 1.03-1.29 (2H; m); 1.387-1.63 (2H; m); 1.72-1.90 (2H; m); 1.90-2.11 (2H; m); 2.35-2.48 (1H; m); 2.52-2.84 (3H; m); 3.39 (3H; s); 3.68-3.84 (1H; m); 3.84-4.02 (2H; m); 7.09 (1H; dd; 9 Hz; 3 Hz); 7.25-7.33 (2H; m); 7.38 (1H; d; 3 Hz); 7.41 (1H; d; 9 Hz); 7.73-7.82 (2H; m). IR (KBr; $cm^{-1}$): 3381; 3203; 1770; 1657.

The invention claimed is:

1. A method for treating obesity, type II diabetes, or irritable bowel disease, for delaying preterm birth, or for causing lipolysis, in a patient in need thereof, comprising administering to the patient an effective amount of a compound of formula (I):

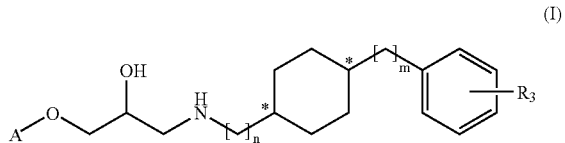

wherein
A is a group of formula (a) or (b)

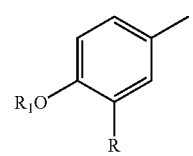

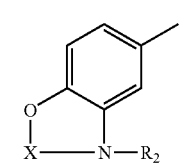

R is a hydrogen or halogen atom, an —S(O)$_z$(C$_1$-C$_4$)alkyl group, an —NHSO$_2$(C$_1$-C$_4$)alkyl group, an —SO$_2$NH(C$_1$-C$_4$)alkyl group, an —NHSO$_2$(C$_1$-C$_4$)alkylene-phenyl group or an —NHSO$_2$phenyl group, wherein the phenyl moiety is optionally substituted with a halogen atom, a (C$_1$-C$_4$)alkyl group or a (C$_1$-C$_4$)alkoxy group;

R$_1$ is a hydrogen atom, a (C$_1$-C$_4$)alkyl group, a —CO(C$_1$-C$_4$)alkyl group, a phenyl-(C$_1$-C$_4$)alkylene group or a —COphenyl group, wherein the phenyl moiety is optionally substituted with a halogen atom or a (C$_1$-C$_4$)alkoxy group;

R$_2$ is a hydrogen atom, an —SO$_2$(C$_1$-C$_4$)alkyl group, an —SO$_2$(C$_1$-C$_4$)alkylene-phenyl group or an —SO$_2$phenyl group;

X taken together with the O and N atoms to which it is attached and the carbon atoms of the phenyl moiety to which the O and N atoms are attached form a 5 to 8 membered ring, wherein the 5 to 8 membered ring is saturated or unsaturated, and is optionally substituted with one or two (C$_1$-C$_4$)alkyl groups or one or two oxo groups;

n, m and z are, independently 0, 1 or 2;

R$_3$ is a hydrogen or halogen atom, a (C$_1$-C$_6$)alkyl group, a (C$_1$-C$_4$)alkoxy group, a —COO(C$_1$-C$_4$)alkyl group, a —CO(C$_1$-C$_4$)alkyl group, an —NHSO$_2$(C$_1$-C$_4$)alkyl group, an —NHSO$_2$phenyl-(C$_1$-C$_4$)alkyl group, —NO$_2$, —CN, —CONR$_4$R$_5$, —COOH, or a 4,5-dihydro-1,3-oxazol-2-yl or 4,4-dimethyl-4,5-dihydro-1,3-oxazol-2-yl group; and R$_4$ and R$_5$ are, independently, a hydrogen atom, a phenyl, a (C$_1$-C$_4$)alkyl group or a phenyl-(C$_1$-C$_4$)alkylene group; or R$_4$ and R$_5$ together with the nitrogen atom to which they are attached, form a 5 to 7 membered ring;

or a salt thereof.

2. The method according to claim 1, wherein for the compound of formula (I), n and m are each 0.

3. The method according to claim 1, wherein for the compound of formula (II), R$_1$ is a hydrogen atom.

4. The method according to claim 1, wherein for the compound of formula (I), R is chosen from an —NHSO$_2$(C$_1$-C$_4$)alkyl group, an —NHSO$_2$phenyl-(C$_1$-C$_4$)alkyl group or an —NHSO$_2$phenyl group.

5. The method according to claim 1, wherein for the compound of formula (I), R$_3$ is —CN, —COOH, —COO(C$_1$-C$_4$)alkyl or —CO(C$_1$-C$_4$)alkyl.

6. The method according to claim 1, wherein for the compound of formula (I), z is 2.

7. The method according to claim 1, wherein the compound of formula (I) is ethyl 4-[4-((2S)-2-hydroxy-3-(4-hydroxy-3-(methylsulphonylamino)phenoxy)propylamino)cyclohexyl]benzoate.

8. The method according to claim 1, wherein the compound of formula (I) is ethyl 4-[4-((2S)-2-hydroxy-3-(4-hydroxy-3-(phenylsulphonylamino)phenoxy)propylamino)cyclohexyl]benzoate.

9. The method according to claim 1, wherein for the compound of formula (I), X is methylene, ethylene or propylene.

10. The method according to claim 1, wherein for the compound of formula (I), X is carbonyl, —CO—CO—, —CO—C((C$_1$-C$_4$)alkyl)$_2$—CO—, —CO—CH$_2$—, or a methylene monosubstituted or disubstituted with (C$_1$-C$_4$) alkyl.

11. The method according to claim 1, wherein the compound of formula (I) is 4-[4-((2S)-2-hydroxy-3-(4-hydroxy-3-(methylsulphonylamino)phenoxy)propylamino)cyclohexyl]benzoic acid.

12. The method according to claim 1, wherein the compound of formula (I) is ethyl 4-[4-((2S)-3-(4-benzyloxy-3-(methylsulphonylamino)phenoxy)-2-hydroxypropylamino)cyclohexyl]benzoate, ethyl 4-[4-((2S)-2-hydroxy-3-(4-hydroxy-3-(n-butylsulphonylamino)phenoxy)propylamino)cyclohexyl]benzoate, ethyl 4-[4-((2S)-2-hydroxy-3-(4-hydroxy-3-(benzylsulphonylamino)phenoxy)propylamino)cyclohexyl]benzoate, ethyl 4-[4-((2S)-2-hydroxy-3-(4-hydroxy-3-(methylsulphonyl)phenoxy)propylamino)cyclohexyl]benzoate, N-[5-[[((2S)-3-((4-(4-(4,4-dimethyl-4,5-dihydro-1,3-oxazol-2-yl)phenyl)cyclohexyl)amino)-2-hydroxypropyl]oxy]-2-hydroxyphenyl]methanesulphonamide, 4-[4-((2S)-2-hydroxy-3-(4-hydroxy-3-(methylsulphonylamino)phenoxy)propylamino)cyclohexyl]-N,N-diethylbenzamide, 4-[4-((2S)-2-hydroxy-3-(4-hydroxy-3-(methylsulphonylamino)phenoxy)propylamino)cyclohexyl]-N-n-butylbenzamide, 4-[4-((2S)-2-hydroxy-3-(4-hydroxy-3-(methylsulphonylamino)phenoxy)propylamino)cyclohexyl]benzene, 4-[4-((2S)-2-hydroxy-3-(4-hydroxy-3-(methylsulphonylamino)phenoxy)propylamino)cyclohexyl]benzonitrile, 4-[4-((2S)-2-hydroxy-3-(4-hydroxy-3-(methylsulphonylaminophenoxy)propylamino)cyclohexyl]benzamide, ethyl 4-[4-((2S)-2-hydroxy-3-(4-methoxy-3-(methylsulphonylamino)phenoxy)propylamino)cyclohexyl]benzoate, ethyl 4-[4-(((2S)-2-hydroxy-3-[(3-(methylsulphonyl)-2-oxo-2,3-dihydro-1,3-benzoxazol-5-yl]oxy)propyl)amino)cyclohexyl]benzoate, ethyl 4-[4-((2S)-2-hydroxy-3-((5-methylsulphonyl-2,3,4,5-tetrahydro-1,5-benzoxazepin-7-yl)oxy)propylamino)cyclohexyl]benzoate, ethyl 4-[4-((2S)-2-hydroxy-3-(4-hydroxy-3-chlorophenoxy)propylamino)cyclohexyl]benzoate, N-[4-[4-((2S)-2-Hydroxy-3-(4-hydroxy-3-methylsulphonylaminophenoxy)propylamino)cyclohexyl]benzoyl]pyrrolidine, ethyl 4-[4-((2S)-2-hydroxy-3-(4-hydroxyphenoxy)propylamino)cyclohexyl]benzoate, 4-[4-((2S)-2-hydroxy-3-(4-hydroxy-3-(methylsulphonylamino)phenoxy)propylamino)cyclohexyl]-1-ethylcarbonylbenzene, tert-butyl 4-[4-((2S)-2-hydroxy-3-(4-hydroxy-3-(methylsulphonylamino)phenoxy)propylamino)cyclohexyl]benzoate, or 4-[4-(((2S)-2-hydroxy-3-[(3-(methylsulphonyl)-2-oxo-2,3-dihydro-1,3-benzoxazol-5-yl]-oxy)propylamino)cyclohexyl]benzamide.

* * * * *